(12) United States Patent
Kim et al.

(10) Patent No.: US 9,113,927 B2
(45) Date of Patent: Aug. 25, 2015

(54) APPARATUS AND METHODS OF USE FOR TREATING BLOOD VESSELS

(75) Inventors: Steven Kim, Los Altos, CA (US); Kyle R. Rick, Boulder, CO (US); Mani N. Prakash, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1139 days.

(21) Appl. No.: 12/696,671

(22) Filed: Jan. 29, 2010

(65) Prior Publication Data

US 2011/0190754 A1 Aug. 4, 2011

(51) Int. Cl.
*A61B 18/18* (2006.01)

(52) U.S. Cl.
CPC ............ *A61B 18/18* (2013.01); *A61B 18/1815* (2013.01); *A61B 2018/1861* (2013.01); *A61B 2018/1869* (2013.01)

(58) Field of Classification Search
CPC .............. A61B 18/1815; A61B 2018/183; A61B 2018/1869; A61B 18/1861
USPC ............................................ 606/41, 158, 159
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 5,122,136 A | 6/1992 | Guglielmi et al. |
| 5,158,561 A | 10/1992 | Bydell et al. |
| 5,282,799 A | 2/1994 | Rydell |
| 5,437,665 A | 8/1995 | Munro |
| 5,540,680 A | 7/1996 | Guglielmi et al. |
| 5,980,519 A | 11/1999 | Hahnen et al. |
| 6,019,757 A | 2/2000 | Scheldrup |
| D424,694 S | 5/2000 | Tetzlaff et al. |
| D425,201 S | 5/2000 | Tetzlaff et al. |
| 6,245,069 B1 | 6/2001 | Gminder |
| 6,254,601 B1 * | 7/2001 | Burbank et al. ................. 606/45 |
| D449,886 S | 10/2001 | Tetzlaff et al. |
| D457,958 S | 5/2002 | Dycus et al. |
| D457,959 S | 5/2002 | Tetzlaff et al. |
| 6,383,183 B1 | 5/2002 | Sekino et al. |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Ronald Hupczey, Jr.

(57) ABSTRACT

An electrosurgical apparatus is provided. The electrosurgical apparatus includes a cannula insertable into a patient and positionable adjacent abnormal tissue. The electrosurgical apparatus includes a microwave antenna that includes a distal end having a radiating section receivable within the cannula and positionable within a patient adjacent abnormal tissue. The microwave antenna is adapted to connect to a source of electrosurgical energy for transmitting electrosurgical energy to the radiating section. A portion of the radiating section substantially encompasses a portion of the abnormal tissue and may be configured to apply pressure thereto. The microwave antenna is actuated to electrocautery treat tissue to reduce blood flow to the abnormal tissue.

12 Claims, 7 Drawing Sheets

(56) References Cited

U.S. PATENT DOCUMENTS

| | | | |
|---|---|---|---|
| 6,640,139 | B1 | 10/2003 | Ueberle |
| 6,659,105 | B2 | 12/2003 | Burbank et al. |
| D496,997 | S | 10/2004 | Dycus et al. |
| D499,181 | S | 11/2004 | Dycus et al. |
| 6,944,490 | B1 | 9/2005 | Chow |
| 7,037,307 | B2 | 5/2006 | Dennis |
| 7,063,682 | B1 | 6/2006 | Whayne et al. |
| D525,361 | S | 7/2006 | Hushka |
| 7,070,595 | B2* | 7/2006 | Ormsby et al. ............ 606/33 |
| D531,311 | S | 10/2006 | Guerra et al. |
| D533,942 | S | 12/2006 | Kerr et al. |
| 7,147,633 | B2* | 12/2006 | Chee et al. ............... 606/41 |
| D535,027 | S | 1/2007 | James et al. |
| 7,179,255 | B2 | 2/2007 | Lettice et al. |
| 7,197,363 | B2* | 3/2007 | Prakash et al. ............ 607/156 |
| D541,418 | S | 4/2007 | Schechter et al. |
| D541,938 | S | 5/2007 | Kerr et al |
| 7,229,418 | B2 | 6/2007 | Burbank et al. |
| 7,270,658 | B2 | 9/2007 | Woloszko et al. |
| 7,318,823 | B2 | 1/2008 | Sharps et al. |
| RE40,156 | E | 3/2008 | Sharps et al. |
| D564,662 | S | 3/2008 | Moses et al. |
| 7,357,801 | B2 | 4/2008 | Burbank et al. |
| 7,387,625 | B2 | 6/2008 | Hovda et al. |
| 7,425,212 | B1 | 9/2008 | Danek et al. |
| 8,202,280 | B2* | 6/2012 | Richter ............... 606/139 |
| 2002/0022837 | A1* | 2/2002 | Mazzocchi et al. ........... 606/41 |
| 2003/0216759 | A1* | 11/2003 | Burbank et al. ............ 606/157 |
| 2007/0198006 | A1 | 8/2007 | Prakash et al. |
| 2007/0219546 | A1 | 9/2007 | Mody et al. |
| 2007/0225701 | A1 | 9/2007 | O'Sullivan |
| 2008/0004615 | A1 | 1/2008 | Woloszko et al. |
| 2009/0192510 | A1 | 7/2009 | Bahney |
| 2012/0232569 | A1* | 9/2012 | Wright ............... 606/158 |
| 2012/0330351 | A1* | 12/2012 | Friedman et al. ........... 606/205 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | WO 03/088858 | 10/2003 |

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.

(56) References Cited

OTHER PUBLICATIONS

U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.

(56) References Cited

OTHER PUBLICATIONS

K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/ Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.

(56) References Cited

OTHER PUBLICATIONS

European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

\* cited by examiner

APPARATUS AND METHODS OF USE FOR TREATING BLOOD VESSELS

BACKGROUND

1. Technical Field

The present disclosure relates to an apparatus and method for treating blood vessels. More particularly, the present disclosure relates to an apparatus including a microwave antenna having a radiating loop configuration that is utilized for treating blood vessels.

2. Background of Related Art

In recent years a number of non-invasive techniques have been developed to repair abnormalities (e.g., aneurysms, arterio-venous fistulas, varicose veins, etc.) occurring in hollow body biological organs and/or vessels. Typically, the non-invasive techniques generally seek to "re-line" the blood flow path through the organ and/or vessel.

For example, in the instance of a vessel afflicted with an aneurysm, endovascular techniques typically involve attempting to form a mass within a sac of the aneurysm. Typically, a microcatheter (or other suitable device) is used to access the aneurysm. More particularly, a distal tip of the microcatheter is placed within a blood vessel (e.g., a parent artery or vein) that is in fluid communication with the sac of the aneurysm. Thereafter, the distal tip of the microcatheter is used to inject embolic material into the sac of the aneurysm. In certain instances, the embolic material may include, for example, detachable coils or an embolic agent.

Disadvantages associated with injecting embolic material into the sac of the aneurysm include migration of the embolic material out of the sac of the aneurysm and into the parent artery afflicted with the aneurysm. Migration of the embolic material can cause permanent and irreversible occlusion of the parent artery. For example, when detachable coils are used to treat, e.g., occlude, an aneurysm, the detachable coils may migrate out of the sac of the aneurysm and into the patient's artery. Moreover, it is, at times, difficult to gauge the exact size of the sac of the aneurysm when the detachable coils are being injected into the sac. Therefore, there is a risk of overfilling the sac of the aneurysm in which case the detachable coils may spill out of the sac of the aneurysm and into the patient's artery, which may result in permanent and irreversible occlusion of the patient's artery. Another disadvantage associated with the use of detachable coils in treating an aneurysm involves coil compaction over time. More particularly, after filling a sac of the aneurysm with detachable coils, space may remain between the detachable coils. Continued hemodynamic forces from blood circulation act to compact the detachable coil mass, which, in turn, may result in a cavity in the aneurysm neck. As a result thereof, the aneurysm may recanalize which, in turn, may lead to blood flowing through the neck of the aneurysm and into the sac of the aneurysm. Embolic agent (e.g., a liquid polymer) migration is also a problem. More particularly, when a liquid polymer is injected into the sac of the aneurysm, it (the liquid polymer) can migrate out of the sac of the aneurysm due to the hemodynamics of the system; this can also lead to irreversible occlusion of the parent vessel.

Another endovascular technique for treating aneurysms involves inserting a detachable balloon (or other suitable device) into a sac of the aneurysm using a microcatheter. In this instance, the detachable balloon is inflated using embolic material, such as liquid polymer material. The balloon is then detached from the microcatheter and left within the sac of the aneurysm in an attempt to fill the sac of the aneurysm and form a thrombotic mass in the aneurysm. However, detachable balloons also suffer disadvantages. For example, detachable balloons, when inflated, typically do not conform to the interior configuration of the aneurysm sac. Instead, the detachable balloon requires the sac of the aneurysm to conform to the exterior surface of the detachable balloon. Thus, there is an increased risk that the detachable balloon will rupture the sac of the aneurysm.

As an alternative to the foregoing endovascular techniques, or in combination therewith, a distal tip of a microwave antenna may be placed within a blood vessel (e.g., an artery or vein) that is in fluid communication with the sac of the aneurysm. In this instance, the microwave antenna and/or distal tip is configured to treat the aneurysm via electrosurgical energy (e.g., RF or microwave energy). More particularly, the distal tip is configured to heat the interior of the sac aneurysm, i.e., heat the blood within the aneurysm, until a thrombus or thrombotic mass is formed.

SUMMARY

The present disclosure provides an electrosurgical apparatus. The electrosurgical apparatus includes a cannula insertable into a patient and positionable adjacent abnormal tissue. The electrosurgical apparatus includes a microwave antenna that includes a distal end having a radiating section receivable within the cannula and positionable within a patient adjacent abnormal tissue. The microwave antenna is adapted to connect to a source of electrosurgical energy for transmitting electrosurgical energy to the radiating section. A portion of the radiating section substantially encompasses a portion of the abnormal tissue and may be configured to apply pressure thereto. The microwave antenna is actuated to electrocautery treat tissue to reduce blood flow to the abnormal tissue.

The present disclosure provides a method for treating various abnormalities associated with blood vessels. The method includes an initial step of positioning a cannula adjacent an abnormal tissue. Inserting a microwave antenna including a radiating section defining a radiating loop into the cannula is a step of the method. In some embodiments, the microwave antenna is adapted to connect to a source of electrosurgical energy for transmitting electrosurgical energy to a portion of the radiating section. A step of the method includes positioning the radiating loop adjacent the abnormal tissue such that the radiating loop applies pressure thereto. Transmitting electrosurgical energy to the radiating loop to treat tissue is another step of the method.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the presently disclosed apparatus and methods are described in detail with reference to the drawing figures wherein like reference numerals identify similar or identical elements. As used herein and as is traditional, the term "distal" refers to the portion which is furthest from the user and the term "proximal" refers to the portion that is closest to the user. In addition, terms such as "above", "below", "forward", "rearward", etc. refer to the orientation of the figures or the direction of components and are simply used for convenience of description.

Figure 1:
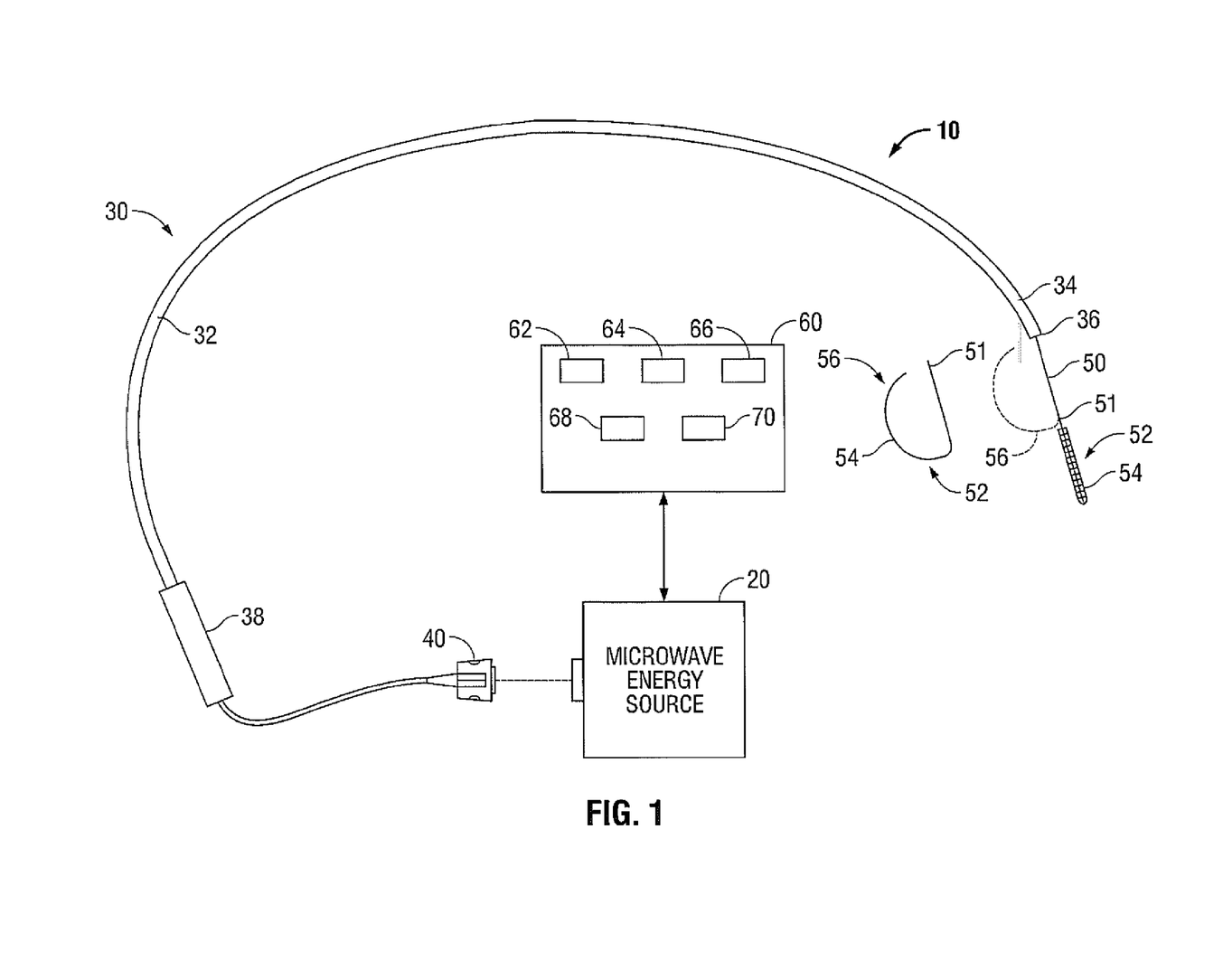
FIG. 1 is a perspective view of a microwave ablation apparatus adapted for use with a microwave antenna that utilizes a deployable loop configuration for treating blood vessels according to an embodiment of the present disclosure.

Referring initially to FIG. 1, a microwave ablation apparatus according to an embodiment of the present disclosure is shown designated 10. As shown, microwave ablation apparatus 10 includes an electrosurgical energy source 20 (e.g., a generator 20 configured to produce RF or microwave electrosurgical energy) that is adapted to connect to a catheter or cannula 30 including a microwave antenna 50 that utilizes a deployable loop configuration for treating blood vessels. Cannula 30 includes a proximal section 32, a distal section 34 including a tip section 36.

Cannula 30 may have any suitable dimensions (e.g., width, height, length, thickness etc.). More particularly, a length of the cannula 30 is typically such that cannula 30 may be readily manipulated by a user and inserted into a body of a patient, either percutaneoulsy, endoluminally, or during an open procedure. By way of example only, the thickness, e.g., diameter, of cannula 30 may also vary depending upon factors that include, but are not limited to, the materials from which cannula 30 is formed, the thickness of microwave antenna 50, the type of procedure, etc.

Proximal section 32 may be formed from any suitable material. More particularly, proximal section 30 may be formed from materials including, but not limited to, medical grade polyolefins, fluoropolymers, polyurethane, or polyvinylidene fluoride. In certain instances, proximal section 32 may be stiffened using stainless steel braided wires, or similar structures, that are arranged to allow proximal section 32 to sustain torque. As is conventional in the art, proximal section 32 may have a relatively high durometer such that proximal section 32 is considered to be relatively "stiff."

A handle 38 is coupled to proximal section 32 in order to enable cannula 30 to be gripped by a user. It should be appreciated, though, that in some embodiments, a handle such as handle 38 that is coupled to proximal section 32 is not necessarily provided. Suitable catheters may also be utilized. In proximity to handle 38 is a connector 40 that is arranged to couple a transmission line (not shown) associated with cannula 30 to a generator 20 (or similar device) that is designed to generate controlled electrosurgical energy, e.g., microwave energy.

Distal end 34 may be operably coupled to the proximal end 32 by any suitable method(s) and/or structure(s). In the illustrated embodiment, distal end 34 (including distal tip 36) is monolithically formed with the proximal end 32. Distal tip 36 may be a relatively sharp to penetrate tissue, e.g., skin, and may include a generally arcuate or curved shape to facilitate positioning of the microwave antenna 50 or portion associated therewith adjacent tissue.

In one embodiment, microwave antenna 50 is configured to be inserted percutaneously into a patient and deployed adjacent a target tissue site, e.g., a target abnormality associated with a blood vessel. With this purpose in mind, microwave antenna 50 is positionable within the cannula 30 and extends along the length of the cannula 30. More particularly, a proximal end 51 of the microwave antenna 50 operably couples to the generator 20 via one or more internal components associated with the handle 38 and/or connector 40. Microwave antenna 50 is movable within the cannula 30 from a non-deployed position (not explicitly shown) to a deployed position (FIG. 1). Microwave antenna 50 may be made from any suitable material, including but not limited to stainless steel, tungsten, copper, etc. In one particular embodiment, a proximal portion 51 of the microwave antenna 50 is a conductive wire or cable made from tungsten. The proximal portion 51 of the microwave antenna 50 may be coated with one or more dielectric materials. In addition, proximal portion 51 may have any suitable shape.

More particularly, a cross-section of the proximal portion 51 may have a circular shape, a half-circular shape, an oval shape, a flat shape, etc. Proximal portion 51 may have any suitable dimensions. In the illustrated embodiment, proximal portion 51 includes a cross-sectional diameter that ranges from about 0.0010 inches to about 0.020 inches. A portion of the microwave antenna 50 is configured to transmit microwave energy to a target tissue site (e.g., a target abnormality associated with a blood vessel). More particularly, a distal end 52 of the microwave antenna 50 is configured to wrap around and contact or squeeze an abnormality associated with a blood vessel. To this end, the distal end 52 is operably coupled to (by any suitable method(s)) and in electrical communication with the proximal end 51 of the microwave antenna 50 and includes a radiating section 54 having a loop configuration ("loop" 56) with a loop diameter of suitable proportion.

In the illustrated embodiment of FIG. 1, radiating section 54 is made from a suitable shape memory alloy, such as, for example, Nitinol (other shape memory alloys may be utilized and are contemplated). As is known in the art, shape memory alloys transition from an initial state to an original or "cold forged" state. In accordance with the present disclosure, radiating section 54 may have any suitable configuration when in an initial state, i.e., a state other than the "cold forged" or "looped" state. More particularly, in an embodiment, the radiating section 54 includes a generally straight or linear configuration (see FIG. 1). Alternatively, the radiating section 54 may be pre-formed (by any suitable method(s)) with a loop 56, shown for illustrative purposes in FIG. 1 unassembled from microwave antenna 50. In this instance, the radiating section 54 may be made from any suitable material including those described above with respect to proximal end 51. Radiating section 54 includes a "cold forged" state having a loop diameter of suitable proportion.

More particularly, a suitable loop diameter is one that is sufficient to fully wrap around or substantially encompass a target abnormality and may be configured to apply a closing or squeezing pressure of suitable proportion to the target abnormality. In one particular embodiment, the loop diameter ranges from about 10 mm to about 20 mm. The combination of wrapping around and squeezing the target abnormality facilitates in providing a desired tissue effect to the target abnormality. For example, wrapping around the target abnormality while applying a predetermined pressure thereto provides a consistent and uniform treatment to the target abnormality.

In accordance with the present disclosure, when electrosurgical energy, e.g., microwave energy, is transmitted to the microwave antenna 50 and, more particularly, to the radiating section 54, the radiating section 54 transitions from its initial state, i.e., its "non-looped" state (FIG. 1) to its original or "looped" state (shown in phantom in FIG. 1). In the looped state, loop 56 wraps around and closes in on or squeezes the target abnormality while applying a pressure of suitable proportion to the target abnormality such that consistent and uniform treatment to the target abnormality is formed.

A radiating section 54 that includes a loop 56 that is transitionable provides a user with the capability of treating target abnormalities with various configurations and/or dimensions, as described in greater detail below. Moreover, a radiating section 54 that includes a loop 56 that is transitionable provides a user with the capability of accessing areas of a patient with limited space, e.g., the cannula only needs to be as big as the diameter of the microwave antenna and not as big as the diameter of the loop 56.

In an alternative embodiment, the radiating section 54 is not made from a shape memory alloy and includes a pre-formed loop configuration that is sufficient to fully surround a target abnormality. A radiating section 54 that is not made from a shape memory alloy and that includes a pre-formed loop configuration functions as described above with respect the radiating section 54 that is made from a shape memory alloy. In the instance where a microwave antenna 50 includes a radiating section 54 (made from either a shape memory alloy or other suitable material) that is pre-formed, the microwave antenna 50 is configured to be positionable within a cannula of suitable proportion, e.g., a cannula having a diameter at least as big as a diameter of the pre-formed loop.

In certain embodiments, a portion of the microwave antenna, e.g., radiating section 54, may be coated with a non-stick material, such as, for example, polytetrafluoroethylene, commonly referred to in the art and sold under the trademark TEFLON®.

The generator 20, the needle cannula and/or the microwave antenna may be in operable communication with one or more image guidance devices 60 (FIG. 1). In one particular embodiment, the image guidance devices are selected from the group consisting of an ultrasound device 62, an x-ray device 64, a fluoroscopy device 66, a cat scan device 68, a computer tomography (CT) device, and magnetic resonance imaging (MRI) device 70, or combination thereof. The image guidance devices and operative features associated therewith are commonly known in the art and as such will not be discussed in detail.

Figure 2A:
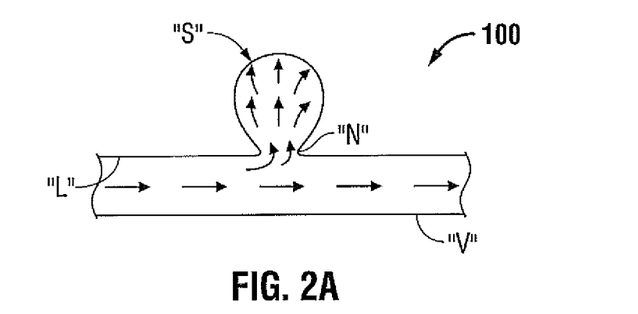
FIGS. 2A-2E are schematic views illustrating a method of use for the microwave apparatus depicted in FIG. 1 in accordance with an embodiment of the present disclosure.
Figure 2B:
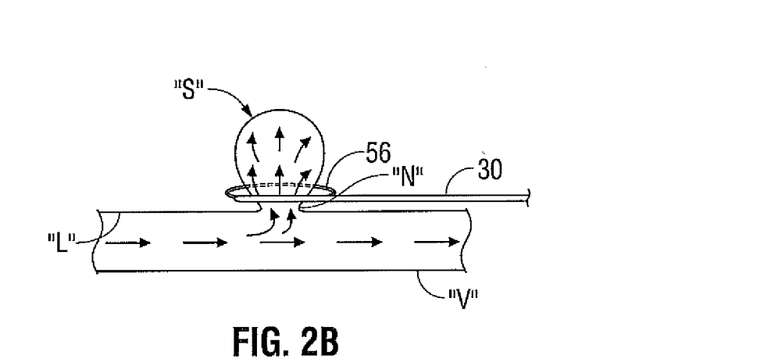
Figure 6:
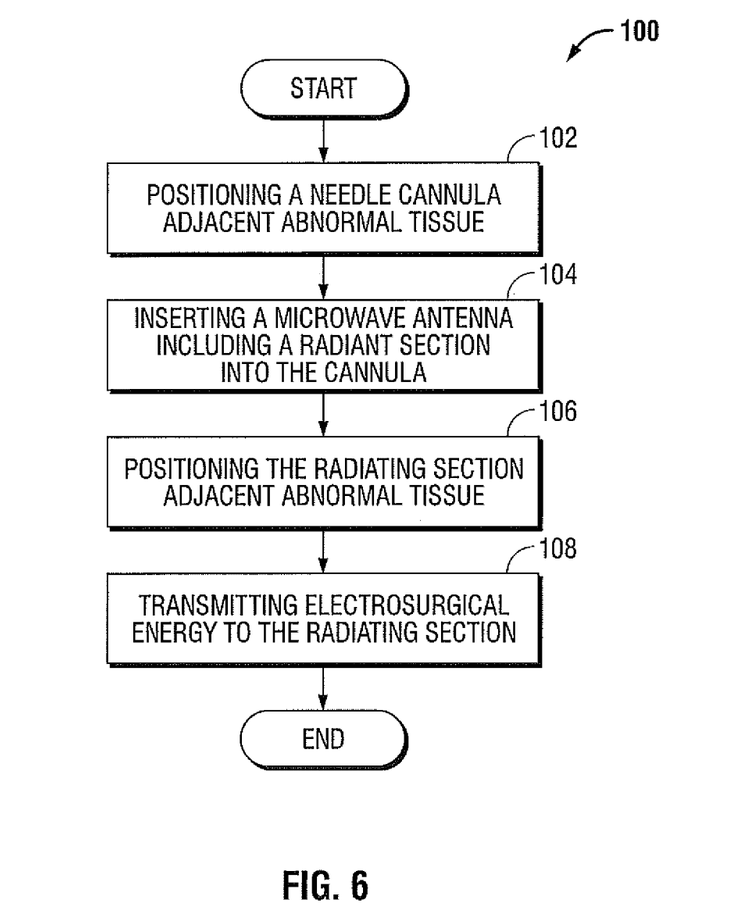
FIG. 6 is a flowchart illustrating a method for treating various blood vessel abnormalities.

With reference to FIGS. 2A-2E, and initially with reference to FIG. 2A, an example operation of microwave ablation apparatus 10 is described. More particularly, the operative features of the microwave antenna 50 are described in terms of use with a method 100 for treating an aneurysm. Typically, an aneurysm develops when a lumen wall "L" of a parent blood vessel "V" weakens. In certain instances, the aneurysm may include a sac "S" and a neck region "N" extending from the lumen wall "L" of the vessel "V," as shown in FIG. 2A. the distal tip 36 of the cannula 30 is percutaneously inserted into a patient and adjacent the aneurysm, see FIG. 6 at step 102. More particularly, the distal tip 36 is positioned adjacent the neck "N" of the aneurysm (FIG. 2B). Thereafter, the distal end 52 including the radiating section 54 of the microwave antenna 50 is inserted into the cannula 30, deployed from the distal tip 36 of the cannula 30 and positioned adjacent the neck "N" of the aneurysm, see FIG. 2B and FIG. 6 at step 104.

Figure 2C:
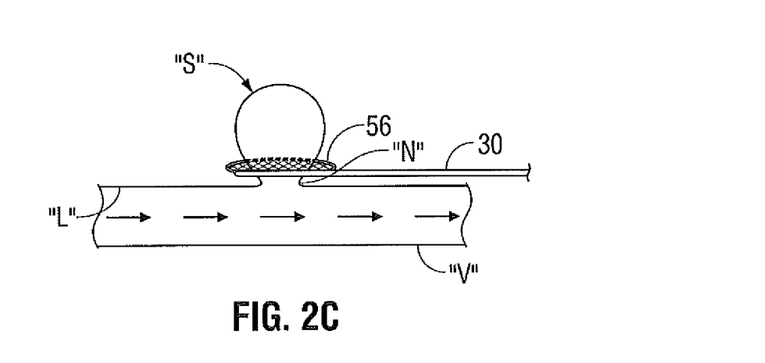
Figure 2D:
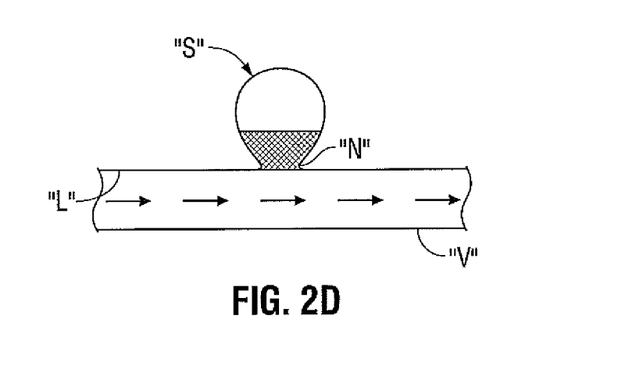
Figure 2E:
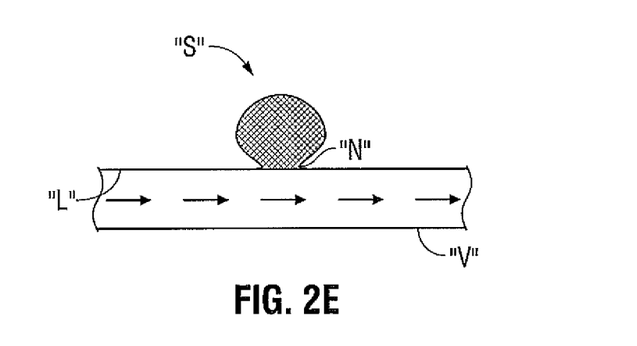

In the illustrated embodiment, the radiating section 54 is made from a shape memory alloy. In this instance, the radiating section 54, or portion thereof, is configured to wrap around and close on or squeeze the neck "N" when electrosurgical energy, e.g., microwave energy, is transmitted to the radiating section 54 (FIG. 2C). More particularly, when the microwave energy is transmitted to the radiating section 54, the radiating section 54 returns to the "cold forged" state forming loop 56 that wraps around and squeezes the neck "N" of the aneurysm, FIG. 6 at step 108. In accordance with the present disclosure, the diameter of loop 56 including the corresponding closure pressure provided therefrom is configured to electrocautery treat (e.g., coagulate, cauterize, etc.) the neck "N" of the aneurysm such that consistent and uniform treatment is formed at the neck "N". As a result thereof, a mass is formed between a portion of the aneurysm and the lumen wall "L" defined by the patient vessel "V." The mass essentially shuts down the neck "N" and/or an opening of the aneurysm "A" such that blood is prevented from flowing into the sac "S" of the aneurysm and is re-lined to the blood flow path, see FIG. 2D, for example. In certain instances, the aneurysm may be severed and, subsequently, removed from the body of the patient. Or, in some instances, the aneurysm may simply shrink to a size that poses no serious threat to the patient, see FIG. 2E.

In the instance where a radiating section 54 of the microwave antenna 50 is pre-formed, the radiating section 55 functions similarly to that of the radiating section 54 described above.

Figure 3A:
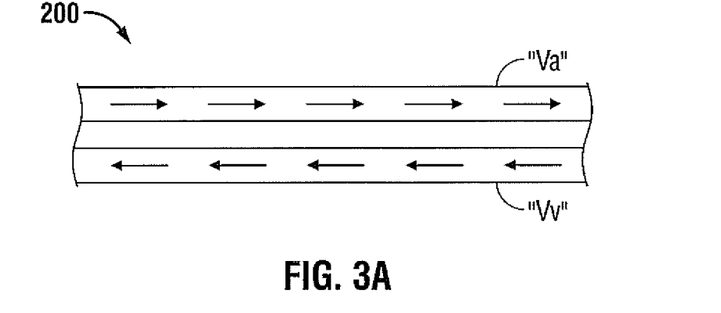
FIGS. 3A-3D are schematic views illustrating a method of use for the microwave apparatus depicted in FIG. 1 in accordance with an alternate embodiment of the present disclosure.
Figure 3B:
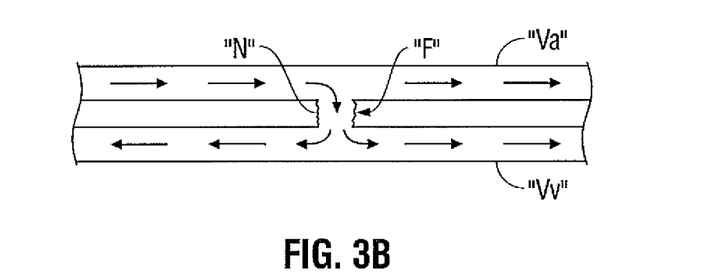

With reference to FIGS. 3A-3D, and initially with reference to FIG. 3A, an example operation of microwave ablation apparatus 10 is described in terms of a method 200 for treating a fistula "F." In a human body, certain types of blood vessels (e.g., artery and vein) are arranged adjacent each other (FIG. 3A). In certain instances, a fistula "F" may develop between a lumen wall of a patient blood vessel "Va" (e.g., an artery) and a lumen wall of another patient vessel "Vv" (e.g., a vein), see FIG. 3B. In certain instances, the fistula "F" may include a neck region "N" extending from the lumen wall of the vessel "Va" to the lumen wall of the vessel "Vv," as shown in FIG. 2A.

Figure 3C:
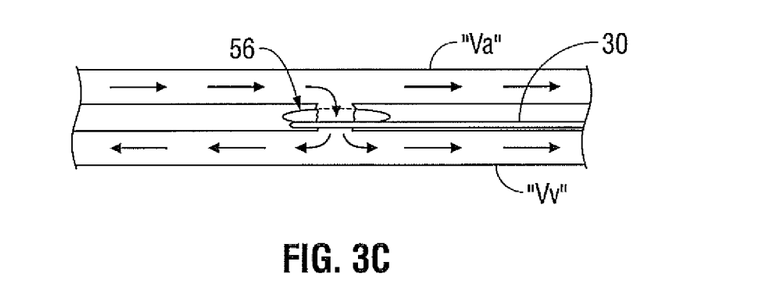

Initially, the distal tip 36 is percutaneously inserted into a patient and adjacent the fistula "F." More particularly, the distal tip 36 is positioned adjacent the neck "N" of the fistula "F" (FIG. 3C). Thereafter, the distal end 52 including the radiating section 54 of the microwave antenna 50 is inserted into the cannula 30, deployed from the distal tip 36 of the cannula 30 and positioned adjacent the neck "N" of the fistula "F," see FIG. 3C.

Figure 3D:
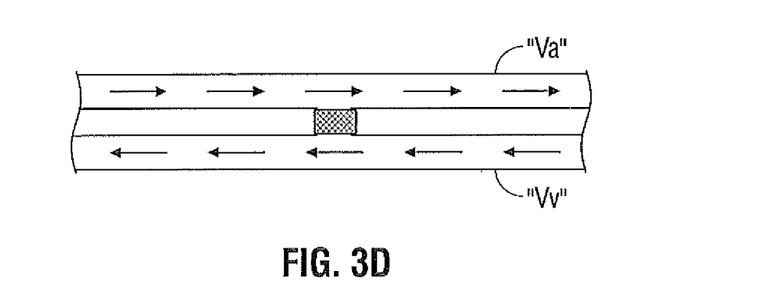

As described above, the radiating section 54 may be made from a shape memory alloy. In this instance, the radiating section 54, or portion thereof, is configured to wrap around the neck "N" when electrosurgical energy, e.g., microwave energy, may be transmitted to the radiating section 54 (FIG. 3C). More particularly, when the microwave energy is transmitted to the radiating section 54, the radiating section 54 returns to the "cold forged" state forming loop 56 that wraps around and squeezes the neck "N" of the fistula "F," FIG. 3C. In accordance with the present disclosure, the diameter of loop 56 including the corresponding closure pressure provided therefrom is configured to treat the neck "N" of the fistula "F" such that a consistent and uniform blockage is formed at the neck "N". As a result thereof, a mass is formed between a portion of the fistula "F" and the lumen wall defined by the vessels "Va" and "Vv." The mass essentially shuts down the neck "N" (and/or openings associated therewith) such that blood is prevented from flowing from one blood vessel, e.g., blood vessel Va, through the neck "N" and to the other blood vessel, e.g., blood vessel Vv, and is re-lined to the blood flow path, see FIG. 3D, for example. In certain instances, the fistula "F" may be severed.

Figure 4A:
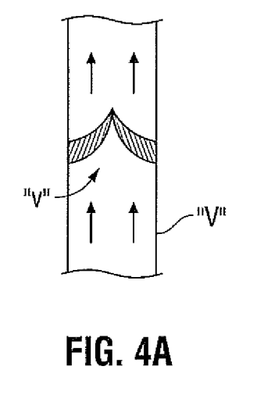
FIGS. 4A-4D are schematic views illustrating a method of use for the microwave apparatus depicted in FIG. 1 in accordance with another embodiment of the present disclosure.
Figure 4B:
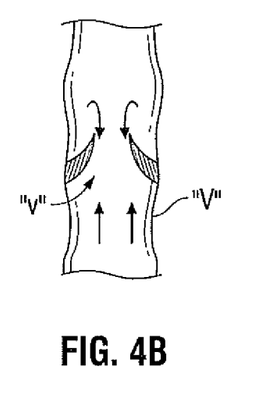

With reference to FIGS. 4A-4D, and initially with reference to FIG. 4A, an example operation of a microwave ablation apparatus 10 is described in terms of a method 300 for treating varicose veins. More particularly, a vein "V" includes leaflet valves "v" that prevent blood from flowing backwards within the vein "V" (FIG. 4A). Typically, a varicose vein develops when the valve "v" extending across lumen wall "L" of the vein "V" weakens. More particularly, when vein "V" become varicose, the leaflets of the valve "v" no longer meet properly and the valve "v" does not close, which allows blood to flow backwards within the vein "V," which, in turn, causes the vein to dilate (FIG. 4B).

Figure 4C:
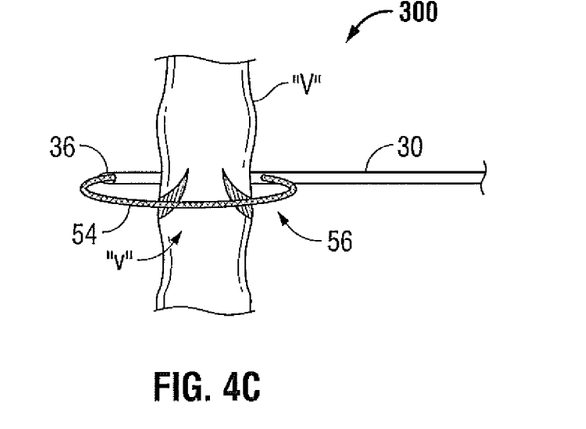
Figure 4D:
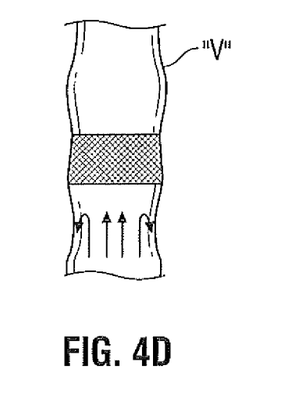

Initially, the distal tip 36 is percutaneously inserted into a patient and adjacent the vein "V." More particularly, the distal tip 36 is positioned adjacent the valve "v" of the vein "V." Thereafter, the distal end 52 including the radiating section 54 of the microwave antenna 50 is inserted into the cannula 30, deployed from the distal tip 36 of the cannula 30 and positioned adjacent the valve "v" of the vein "V," see FIG. 4C. As described above, the radiating section 54 may be made from a shape memory alloy. In this instance, the radiating section 54, or portion thereof, is configured to wrap around the vein "V" adjacent valve "v" when electrosurgical energy, e.g., microwave energy, is transmitted to the radiating section 54 (FIG. 4C). More particularly, when the microwave energy is transmitted to the radiating section 54, the radiating section 54 returns to the "cold forged" state forming loop 56 that wraps around and squeezes the vein "V" in the proximity of the valve "v" (FIG. 4C). In accordance with the present disclosure, the diameter of loop 56 including a corresponding closure pressure provided therefrom is configured to close off the valve "v" and/or the vein "V" such that a consistent and uniform blockage is formed at the valve "v" and/or vein "V." As a result thereof, a mass is formed in the vein "V" at the valve "v." The mass essentially shuts down the valve "v" and/or the vein "V" such that blood is prevented from flowing through the vein "V." With the vein "V" blocked, i.e., inoperable, other veins in the proximate area can take over.

Figure 5A:
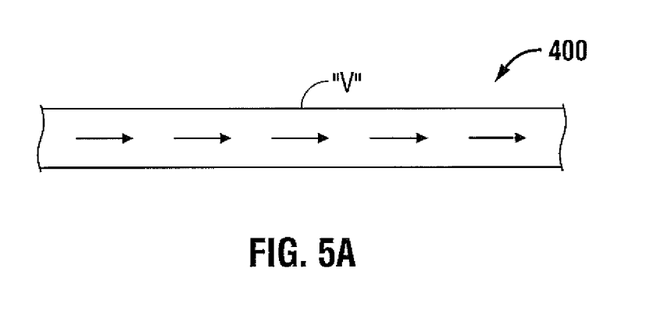
FIGS. 5A-5C are schematic views illustrating a method of use for the microwave apparatus depicted in FIG. 1 in accordance with yet another embodiment of the present disclosure.
Figure 5B:
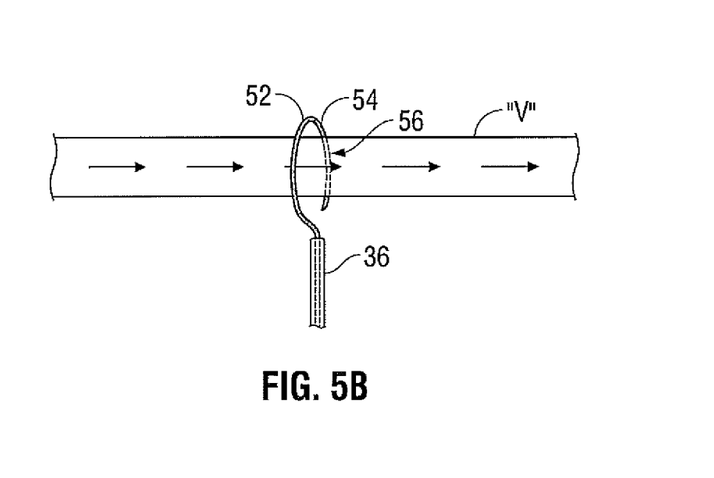
Figure 5C:
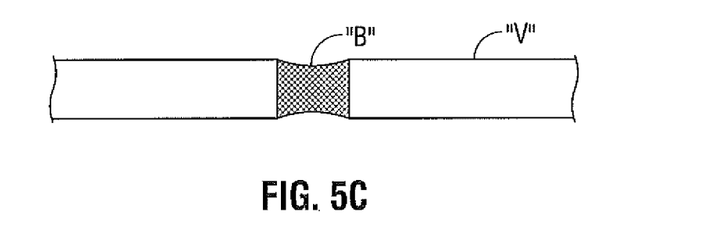

With reference to FIGS. 5A-5C, and initially with reference to FIG. 5A, an example operation of microwave ablation apparatus 10 is described in terms of a method 400 for treating a blood vessel "V." Initially, the distal tip 36 is percutaneously inserted into a patient and adjacent the vein "V." More particularly, the distal tip 36 is positioned adjacent the blood vessel "V." Thereafter, the distal end 52 including the radiating section 54 of the microwave antenna 50 is inserted into the cannula 30, deployed from the distal tip 36 of the cannula 30 and positioned adjacent the blood vessel "V," see FIG. 5B. As described above, the radiating section 54 may be made from a shape memory alloy. In this instance, when the microwave energy is transmitted to the radiating section 54, the radiating section 54 returns to the "cold forged" state forming loop 56 that wraps around and squeezes the blood vessel "V" (FIG. 5B). In accordance with the present disclosure, the diameter of loop 56 including a corresponding closure pressure provided therefrom is configured to seal the blood vessel "V" such that a consistent and uniform blockage "B" is formed at the blood vessel "V," FIG. 5C. As a result thereof, a mass is formed at the blood vessel "V." In this embodiment, a suitable closure pressure may be from about 3 kg/cm$^2$ to about 16 kg/cm$^2$.

From the foregoing and with reference to the various figure drawings, those skilled in the art will appreciate that certain modifications can also be made to the present disclosure without departing from the scope of the same. For example, one or more modules associated with the generator 200 may be configured to monitor one or more electrical parameters, e.g., impedance, power, current, voltage, etc., associated with the radiating section 54 of the microwave antenna 50 while the radiating section 54 is treating tissue at a target tissue site, e.g., at the target aneurysm. More particularly, one or more sensors may be operably disposed adjacent the aneurysm and in operative communication with the module(s) associated with the generator 200. In this instance, for example, the sensor(s) may provide data pertaining to impedance of the microwave antenna 50 (or operative component associated therewith, e.g., radiating section 54) or the aneurysm during treatment of the aneurysm. In this instance, the sensor(s) may be configured to trigger a control signal to the module(s) when predetermined threshold impedance that corresponds to a specific aneurysm type or size is reached and/or detected. When the module(s) detects a control signal, the module may send a command signal to the generator 200 such that the electrosurgical power output to the microwave antenna 50 may be adjusted accordingly.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical apparatus, comprising:
a cannula;
a microwave antenna including a distal end having a radiating section movably disposed within the cannula and positionable within a patient adjacent abnormal tissue, the microwave antenna adapted to connect to a source of electrosurgical energy for transmitting electrosurgical energy to the radiating section to both treat tissue and to transition the radiating section from a first state having a longitudinal configuration to a second state having a looped configuration; and
a sensor associated with the radiating section configured to monitor an electrical control parameter associated with the radiating section, the electrical control parameter selected from the group consisting of impedance, power, current, and voltage,
wherein the radiating section is configured to remain in the first state while positioned adjacent abnormal tissue until the electrosurgical energy is transmitted to the radiating section to controllably transition the radiating section to the second state.

2. An electrosurgical apparatus according to claim 1, wherein at least a portion of the radiating section includes a cross-section area having a configuration selected from the group consisting of circular, flat and oval.

3. An electrosurgical apparatus according to claim 1, wherein the microwave antenna is percutaneously positionable within a patient adjacent abnormal tissue.

4. An electrosurgical apparatus according to claim 3, wherein at least one of the cannula or the microwave antenna is in operable communication with an image guidance device selected from the group consisting of an ultrasound device, an x-ray device, a fluoroscopy device, a cat scan device, a computer tomography (CT) device and a magnetic resonance imaging (MRI) device.

5. An electrosurgical apparatus according to claim 1, wherein the radiating section is formed from a shape memory alloy.

6. An electrosurgical apparatus according to claim 5, wherein the shape memory alloy is Nitinol.

7. An electrosurgical apparatus according to claim 5, wherein the shape memory alloy is cold forged to form a radiating loop section that provides a closure pressure about tissue that ranges from 3 kg/cm² to 16 kg/cm².

8. An electrosurgical apparatus according to claim 1, wherein the radiating section is positionable adjacent abnormal tissue selected from the group consisting of aneurysms, fistulas and non-functional valves.

9. A method for treating various abnormalities associated with blood vessels, comprising:
   inserting a microwave antenna including a radiating section into a cannula, the microwave antenna adapted to connect to a source of electrosurgical energy for transmitting electrosurgical energy to at least a portion of the radiating section;
   transmitting electrosurgical energy to the radiating section to both treat abnormal tissue and to transition the radiating section from a first state having a longitudinal configuration to a second state having a looped configuration to encompass abnormal tissue adjacent the radiating section, the radiating section remaining in the first state while positioned adjacent abnormal tissue until the electrosurgical energy is transmitted to the radiating section to controllably transition the radiating section to the second state;
   sensing an electrical control parameter associated with the radiating section selected from the group consisting of impedance, power, current, and voltage; and
   triggering a control signal to the source of electrosurgical energy.

10. A method according to claim 9, further comprising applying uniform pressure to abnormal tissue adjacent the radiating section.

11. A method according to claim 9, further including severing at least a portion of the treated tissue.

12. A method according to claim 9, wherein transmitting electrosurgical energy includes transmitting microwave energy.

* * * * *